United States Patent [19]

Cojean et al.

[11] Patent Number: 5,817,930
[45] Date of Patent: Oct. 6, 1998

[54] PROCESS FOR MEASURING AT LEAST ONE ELEMENT CHOSEN FROM AMONG PU (IV) PU (VI), URANIUM AND NITRATES PRESENT IN A SOLUTION BY LIQUID PHASE CHROMATOGRAPHY

[75] Inventors: Joël Cojean, Bagnols/Ceze; Michel Daubizit, Avignon, both of France

[73] Assignee: Compagnie Generale Des Matieres Nucleaires, Velizy Villacoublay, France

[21] Appl. No.: 806,842

[22] Filed: Feb. 26, 1997

[30] Foreign Application Priority Data

Mar. 13, 1996 [FR] France .................................. 96 03146

[51] Int. Cl.$^6$ .................................................. G01N 30/00
[52] U.S. Cl. .......................................... 73/61.52; 210/656
[58] Field of Search ............................... 73/61.52, 54.08, 73/61.48; 210/656, 198.2

[56] References Cited

FOREIGN PATENT DOCUMENTS 2691542  11/1993  France ........................... G01N 30/02

OTHER PUBLICATIONS

Analusis, vol. 15, No. 5, 1987, pp. 209–216, XP002020165, J.P. Muller: "Determination de l'uranium dans les solutions de retraitement des combustibles irradies par chromatographie en phase liquide".

Journal of Chromatography, vol. 16, No 7, 1993, Science N1, pp. 1589–1599, XP000610888, M. Riaz: "Assay if uranium in the presence of various interfering ions using ion–pair liquid–chromatography".

Chromaatogrphia, vol. 42, No. 1/2, Jan. 1996, Friedr. Vieweg & Sohn, pp. 34–38, XP000610896, S. B. Butt et al.: "Simultaneous assay of cooper iron and uranium in phosphate media by ion–pair liquid chromatography".

National Technical Information Service U.S. Department of Commerce, Springfield, US, Accession #DE92040358/XAB 17 Juillet 92, NTIS data base, Y.C. Rogers et al., "Quantitative analysis of Pu and U using reversed–phase liquid chromatography and spectrophotometric detection".

*Primary Examiner*—Hezrone E. Williams
*Assistant Examiner*—Jay L. Politzer
*Attorney, Agent, or Firm*—Pearne, Gordon, McCoy and Granger LLP

[57] ABSTRACT

The invention concerns a chromatographic measurement. The aim of the invention is to measure at least one of the elements chosen from among Pu (IV), Pu (VI), uranium and nitrates, present in a solution by liquid phase chromatography. This aim is attained by a process comprising the following stages:

a) injection of a sample of the solution on a stationary phase comprising an apolar-type support, b) elution by a mobile liquid phase which comprises a counter-ion of ammonium type, sulfate ion, an acid of a normality equal to or greater than 0.001 N, a mixture of solvents comprising an alcohol in $C_1$–$C_4$, a polar modifying organic solvent different from an alcohol, miscible with water, and water, in order to obtain an eluate, and c) analysis of the eluate so as to determine the element(s) present.

11 Claims, 2 Drawing Sheets

PROCESS FOR MEASURING AT LEAST ONE ELEMENT CHOSEN FROM AMONG PU (IV) PU (VI), URANIUM AND NITRATES PRESENT IN A SOLUTION BY LIQUID PHASE CHROMATOGRAPHY

DESCRIPTION

1. Technical Field

This invention concerns a process for measuring at least one of the so-called elements of interest chosen from among plutonium Pu (IV), plutonium Pu (VI), uranium and nitrates, present in aqueous solutions or certain organic matrixes. It particularly applies to the measurement of Pu (IV), Pu (VI), uranium and total nitrates, even in the state of traces, in the various solutions of a nuclear waste fuel reprocessing plant, such as solutions with a high uranium or plutonium content (from 3 to 500 g/l) like dissolution solutions of irradiated fuels, oxalic bittern, plutonium concentrates, fission product concentrates, weighted solutions and solutions with a low uranium and plutonium content (from 0.003 to 2 g/l), like pure uranium, plutonium and nitric acid solutions, fuel decanning solutions, dissolution solutions of plutonium oxide, solutions of effluent treatment plants, fission product solutions, carbonate treatment solutions of organic solvents, purified organic solvents and solutions issuing from uranium extraction columns, etc.

The invention also applies to the measurement of uranium in other types of solutions such as sulfochromic bath solutions, tripolyphosphate solutions, dissolution solutions of uranium ores, river water, physiological liquids, etc.

2. State of the Prior Art

Up to now, in nuclear waste reprocessing plants, measurements of Pu (IV), Pu (VI), uranium and nitrates have been carried out, among other ways, by potentriometric, pH-metric, or spectrophotometric measurement, isotopic dilution, alpha ray spectrometry, spectrofluorimetry, plasma source emission spectrometry, liquid phase chromatography, laser fluorimetry and hybrid x-ray fluorescence.

However, none of these methods are suited to the simultaneous measurement of at least two of the elements of interest chosen from among Pu (IV), Pu (VI), uranium and nitrates, this being the case in a wide range of concentrations.

A process for measuring uranium by liquid phase chromatography is described, for example, by J. P. Muller et al. in ANALUSIS, 1987, vol. 15/no. 5, pp. 209–216. This process consists in retaining the uranium in the form of a pair of ions made up of uranyl trinitrate anion and tetrahexylammonium cation on a silica-grafted stationary phase, eluting the uranium by a mobile phase containing acetonitrile, water and an ion developer such as sulfate, and then in detecting the uranium leaving the column by ultraviolet spectrophotometry at 254 nm. This article also cites the possibility of using a water/methanol mixture as mobile phase. It is also pointed out that Pu (VI) disturbs the chromatograms but that it is possible to overcome this problem by adding ascorbic acid to the diluted sample before injection, which said acid selectively reduces the plutonium. However, this method is not applicable to the simultaneous measurement of plutonium and uranium by liquid phase chromatography, and does not detect uranium in small concentrations.

An improvement to this technique has been proposed in Patent FR-A-2 691 542 which describes a process for measuring uranium alone, consisting in injecting the sample to be measured in a chromatography column filled with an apolar stationary phase and passed by a mobile phase containing cetyltrimethylammonium, a sulfate anion and a solvent favoring the presence of uranium in uranyl trinitrate form, and then in determining the quantity of uranium leaving the column by ultraviolet spectrophotometry. The solvent is made up of acetonitrile and water, to which trifluoracetic acid may be added, permitting a reduction of the uranium peak retention time. But this method does not allow simultaneous measurement of plutonium and uranium by liquid phase chromatography.

Thus, the known processes are applicable neither to the measurement of plutonium by liquid phase chromatography nor to the simultaneous measurement of Pu (IV), Pu (VI), uranium and nitrates.

DISCLOSURE OF THE INVENTION

The invention specifically concerns a process for measuring at least one of the elements chosen from among Pu (IV), Pu (VI), uranium and nitrates by liquid phase chromatography, which may be used for the simultaneous measurement of these elements with good levels of accuracy and reproducibility in a wide range of concentrations (from 450 g/l to 0.001 g/l provided that the detector is sufficiently sensitive). This process may also be applied to the simultaneous measurement of plutonium valences IV and VI, even at low concentrations.

According to the invention, this process for measuring, by liquid phase chromatography, at least one of the elements chosen from among Pu (IV), Pu (VI), uranium and nitrates, present in a solution, comprises the following stages:

a) injection of a sample of the solution on a stationary phase comprising an apolar-type support, b) elution of said sample by a mobile liquid phase which comprises a counter-ion of ammonium type, sulfate ion, an acid of a normality equal to or greater than 0.001N, a mixture of solvents comprising an alcohol in $C_1$–$C_4$ (from one to four carbon atoms), a polar modifying organic solvent different from an alcohol, miscible with water, and water, in order to obtain an eluate, and c) measurement of the eluate so as to determine the element(s) present in the solution to be analyzed and to measure and dose this element or these elements.

In this process, the composition of the mobile phase constitutes an important element. Indeed, the use of a mobile phase comprising a counter-ion of ammonium type makes it possible to transform the apolar stationary phase into a dynamic anionic exchanger. The presence of this quaternary ammonium also permits the pairing of ions with the anionic complexes of plutonium, uranium and nitrates. The counter-ion of ammonium type used may be cetyltrimethylammonium ion and it may be introduced in the mobile phase in the form of salt or hydroxide, preferably the latter.

In this mobile phase, the use of a sulfate in soluble form, for example ammonium sulfate, allows the formation of anionic complexes of plutonium IV and VI and of uranium which will be retained by the apolar stationary phase transformed into dynamic anionic exchanger.

Moreover, an acid such as sulfuric acid of normality equal to or greater than 0.001N is preferentially used to adjust the pH of the liquid mobile phase to an appropriate value so as to avoid the polymerization of plutonium on the column and in the mobile phase. The pH of the liquid mobile phase may be adjusted by any mineral or organic acid other than sulfuric acid provided that this acid does not interfere with the chromatographic mechanism or the detection. However, mineral acids such as phosphoric acid and halogen hydrogen acids are not recommended as they then constitute a considerable handicap in the treatment of effluents. The same holds true for nitric acid since it increases the absorbance of the ultraviolet mobile phase and perturbs the anionic complexation of plutonium by the sulfates.

The alcohol and the other organic solvent present in the mobile phase are polar modifiers which permit the adjustment of the polarity of the mobile phase:

The alcohol has a proton acceptor-type action mechanism on the solutes of the sample to be measured and modifies the selectivity of the elution peaks, particularly in the case of plutonium, in relation to the other elements to be measured. The alcohol used is an alcohol of low molecular weight comprising 1 to 4 carbon atoms ($C_1$–$C_4$) so as to remain totally miscible with water. It may be chosen from among methanol, ethanol, propanol-1 and propanol-2, preferably methanol.

The other polar modifying organic solvent different from an alcohol miscible with water is a polar modifier which acts according to a different mechanism, for example proton donor, or by dipole-dipole interaction on the solutes. This type of polar modifier is added to the mobile phase in order to reduce the retention time of the measured species and consequently of the measurement time. It also makes it possible to retain a selectivity between the peaks which is better than that which would have been obtained by simply increasing the proportion of methanol. A polar modifier with dipole-dipole interactions is preferentially used; this may be chosen from among tetrahydrofurane and dioxane, preferably the former. Other solvents, miscible with water and presenting the same solvation properties, may also be used.

The mobile liquid phase also comprises water.

The chromatography column is filled with an apolar-type stationary phase constituted, for example, by a silica support rendered apolar by an appropriate grafting, a polymeric support and a carbon-based support; a C1 grafted silica support is preferentially used. This apolar stationary phase ensures the retention of the pairs of ions formed from the ammonium-type counter-ion and from the anions comprising the compounds of interest to be measured.

Owing to variations in the characteristics of columns prepared by manufacturers, the composition of the mobile phase sometimes has to be adapted in order to obtain a good selectivity of the elution peaks on the chromatogram of the measured elements and an appropriate duration of analysis. The characteristics of stationary phases possessing a same grafting may in fact vary from one manufacturer to another, for example due to the variation of the diameter of the silica grain pores, to the grafting rate, to the greater or lesser degree of polymerization of the grafted sites, etc.

The constituents of the mobile phase always remain the same but their concentrations or proportions vary.

In addition, for the measurement of certain solutions, it is necessary to choose a mobile phase composition permitting elimination of the parasite peaks which hinder the integration of the Pu (IV) peak. Indeed, the dissolution solutions of irradiated fuels contain numerous elements coming from uranium or plutonium fission and giving rise to small parasite peaks which hinder the integration of the Pu (IV) peak. The mobile phase composition therefore has to be modified in order to measure these solutions.

For example, the liquid mobile phase may comprise in volume:

about 60 to 65% of water,
about 30% of methanol, and
about 5 to 10% of tetrahydrofurane, and may contain about:

0.05 mol/l of sulfuric acid,
0.1 to 0.2 mol/l of ammonium sulfate, and
0.005 mol/l of cetyltrimethylammonium.

In order to remedy the problems encountered, such as the presence of parasite peaks which hinder the integration of the peaks, the variation of the characteristics of columns prepared by manufacturers or the type of species to be measured, the proportions of the constituents of the mobile phase have to be adjusted. If for example, the measurement of plutonium VI is not requested, the composition of the mobile phase may be adjusted so as to reduce the time of analysis.

In order to implement the process of the invention, the following operation may be used:

First of all, the sample of the solution to be measured may be diluted in water, in $HNO_3$ 0.01N, in $H_2SO_4$ 0.01N, in the mobile phase or in a buffer mobile phase which may contain appropriate additives chosen in function of the nature of the solution to be measured. As an example, mention may be made of the case of solutions containing plutonium of valence VI or III, and provided that the plutonium VI is not a compound of interest, where it is advantageous to dilute the sample in a ferrous sulfate solution in order to bring the plutonium to valence IV. For reducing solutions such as plutonium III in hydrazine and hydroxylamine, a treatment with ferric iron will be more appropriate. The dilution rates may vary in a wide range and, in particular, depend on the content and quality of the ions to be measured. The dilution rate will in particular depend on the concentration of the compounds of interest, notably of the compound with the lowest content, and will also be conditioned by the pH. In fact, the pH of the diluted sample to be analyzed must be greater than 1 and less than 8 if silica-based columns are used.

In the first stage, the sample, whether or not diluted, is injected in the column through which the mobile phase passes continuously in order to fix the compounds of interest on an apolar support.

In the second stage, elution of the compounds of interest is carried out by means of the mobile phase. In this second stage, the composition of the mobile phase may be the same or be modified in order to optimize the retention times of each compound of interest. This optimization will be function of the columns applied, a mobile phase used for a C1 grafted silica column being different, for example, from that used for a polymeric resin column, and of the nature of the ions to be analyzed: if, for example, only the uranium/plutonium (IV) pair is of interest, it is advantageous to prefer more eluant mobile phases.

In the third stage, the compounds of interest in the eluate are submitted to qualitative and/or quantitative analysis. According to a preferred mode of application of the process, the analysis will be a spectrophotometric analysis at a wavelength selected in function of the nature of the solution and of the nature and quantity of the elements to be measured. The most commonly used wavelength is 254 nm, but when high sensitivity is required, particularly for nitrate ions, a wavelength of 230 nm may be used, and if it is desired to measure plutonium of valence VI only, it is possible to use a wavelength of 830 nm.

The process of the invention may be applied in standard chromatography appliances comprising:

a chromatographic pump guaranteeing for example rates of from 0.05 to 10 ml/min, for example 1 ml/min, one or more injection valves each including a different sampling loop, for example of 1 and 20 μl, a chromatography column, filled for example with a stationary phase of C1 grafted silica of 3 μm granulometry, having a length of 100 mm and an inner diameter of 4.6 mm, a spectrophotometric detector working at a wavelength of, for example, 254 nm, and a data acquisition device for integration of the chromatogram and piloting.

Other characteristics and advantages of the invention will become more apparent from a reading of the ensuing description, provided for purely illustrative and non-limitative purposes, with reference to the accompanying drawings.

DETAILED DISCLOSURE OF AN EMBODIMENT OF THE INVENTION

Figure 1:
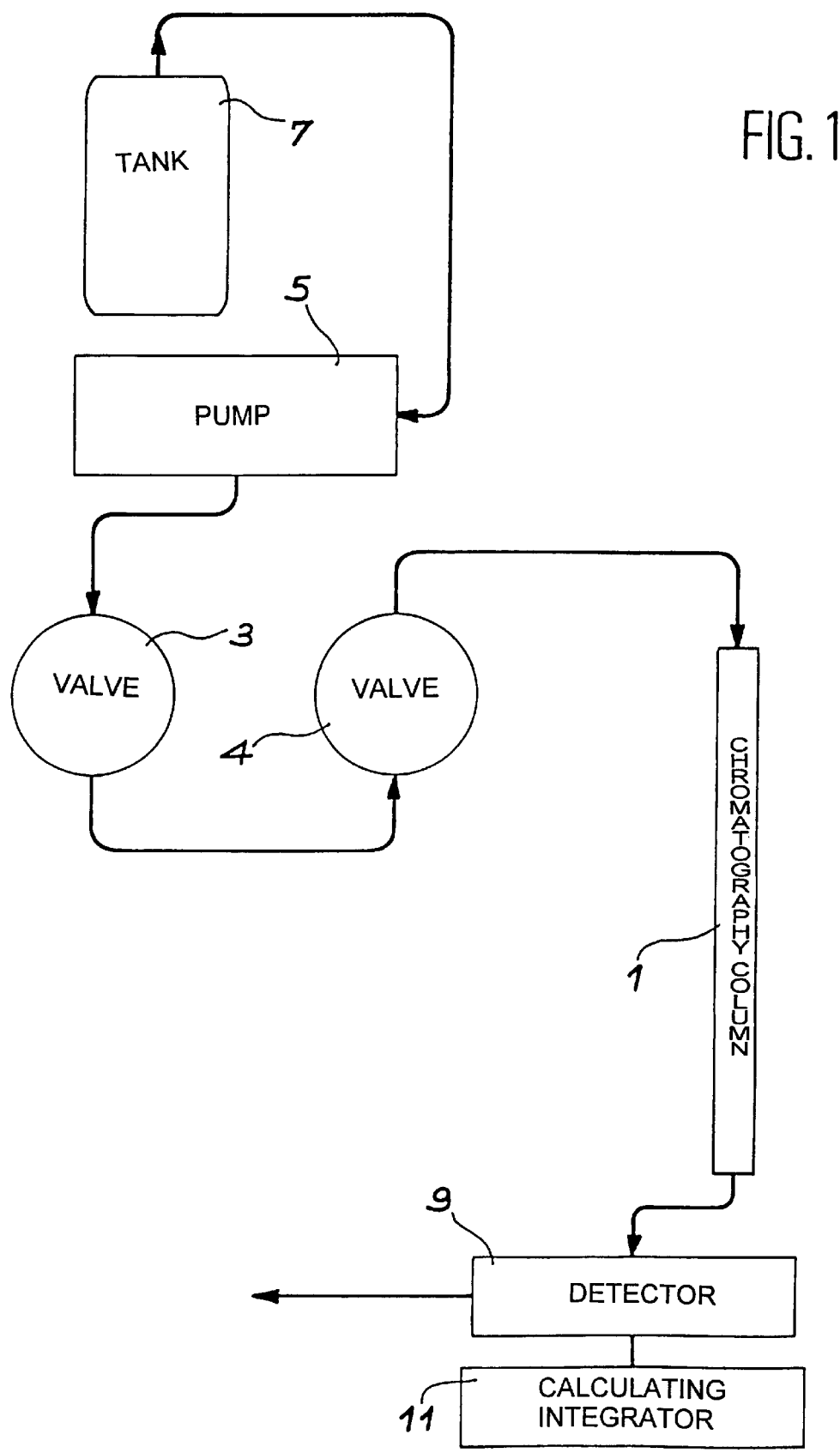
FIG. 1 represents a chromatographic appliance, with one column; for the measurement of plutonium IV, plutonium VI, uranium and nitrates present in solutions.

It may be seen from FIG. 1 that the chromatographic appliance comprises a chromatography column 1 in which a sample is introduced through one of the two injection valves 3 and 4, each fitted with an internal or external loop for sampling the required volume. The first valve 3, with a reduced injection volume, is generally reserved for so-called concentrated solutions, for example:

uranium >50 mg/l, plutonium >50 mg/l, nitrates >50 mg/l.

The second valve 4, with a larger injection volume, is generally reserved for so-called solutions in traces, for example:

uranium <200 mg/l, plutonium <200 mg/l, nitrates <200 mg/l.

These two valves are linked by means of a pump 5 to a mobile phase tank 7. At the exit of the column, the compounds of interest are detected by means of the spectrophotometric detector 9 associated with a calculating integrator 11.

The appliance represented in FIG. 1 is used for measuring the compounds of interest in an aqueous solution, using a mobile phase with the following composition:

60% water,

30% ethanol,

10% tetrahydrofurane.

and containing:

0.05 mol/l of sulfuric acid, 0.1 mol/l of ammonium sulfate, 0.005 mol/l of cetyltrimethylammonium. In this case, a sample of 0.5 ml of the solution to be measured is first of all diluted by 9.5 ml of a nitric acid solution at 0.01 mol/l, then 1 μl of the sample is injected in the chromatography column through the valve 3. The mobile phase is circulated in the column at a rate of 1 ml/min, the column has a length of 100 mm and an inner diameter of 4.6 mm, and is filled with a stationary phase with a type C1 grafted silica base of granulometry 3 μm.

The denomination C1 is a commercial denomination corresponding to a methyl grafting on silanol sites present at the surface and in the pores of the silica grains of the stationary phase. Depending on the reagents used during the preparation of the stationary phase, the functional groupings present on the silica grains are of three types:

$\equiv$Si—CH$_3$, $=$Si(CH$_3$)$_2$,

—Si(CH$_3$)$_3$.

At the exit of the column, the spectrophotometric detector 9 detects the peaks corresponding to plutonium (IV), plutonium (VI), uranium and nitrate ions, and the surface of these peaks is measured with the integrator 11.

Figure 2:
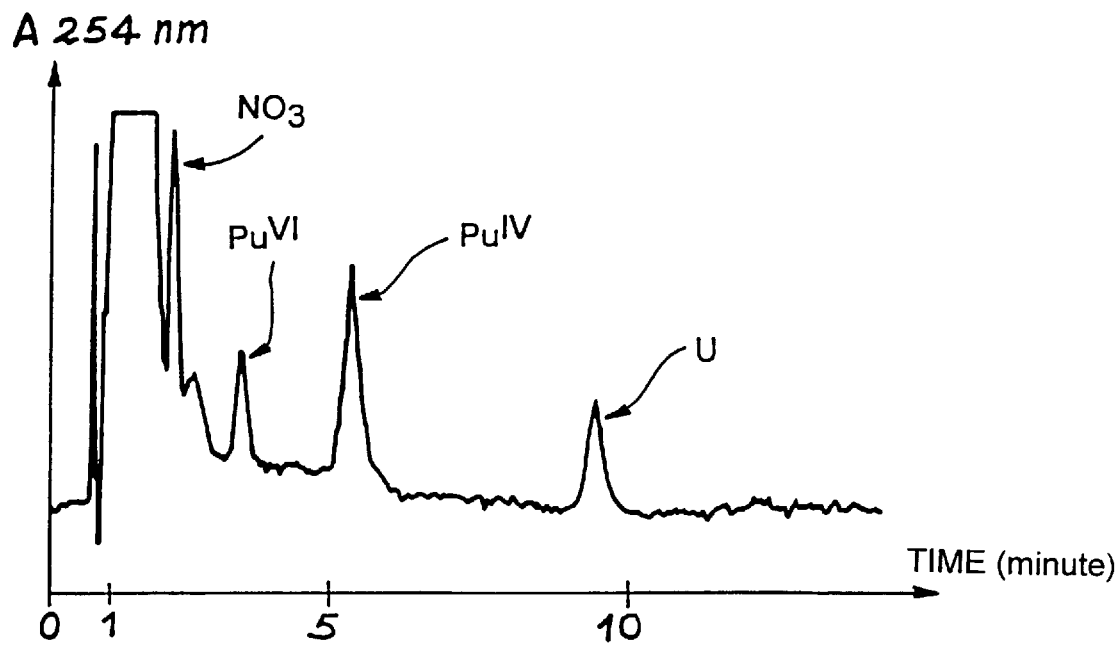
FIG. 2 represents a chromatogram of a solution of a mixture of uranium and plutonium obtained with the measurement method described in this invention.

FIG. 2 is the chromatogram obtained in these conditions, showing on the abscissa the elution times of the different compounds of interest: these are of the order of 3.2 min for the nitrate, 4.2 min for the plutonium (VI), 5.5 min for the plutonium (IV) and 9.5 min for the uranium (VI).

Calibration curves are used for the quantitative analysis, which said curves are obtained by carrying out the same operations on samples whose concentrations in elements of interest are known, and in this way the content of each element in the analyzed sample is determined.

The same measurement may be carried out on an organic solution comprising, for example, tributylphosphate, containing the elements of interest, but in this case, after dilution of the sample by a solution of nitric acid at 0.01 mol/l, or by a solution of sulfuric acid at 0.01 mol/l, or by the mobile phase, the dilution is shaken well and left to decant before injection of for example 1 μl of the lower phase, the remaining operations being performed in the same way.

The confidence interval of the analysis result has for amplitude in relation to the 95% confidence level:

Uranium (+/−) 0.5% for uranium concentrations greater than 1 g/l, and (+/−) 2% for uranium concentrations less than 1 g/l.

Plutonium (+/−) 1% for plutonium concentrations greater than 1 g/l, and 5% for plutonium concentrations less than 1 g/l.

Nitrates (+/−) 0.5% for concentrations greater than 1 g/l, and (+/−) 2% for concentrations less than 1 g/l.

Figure 3:
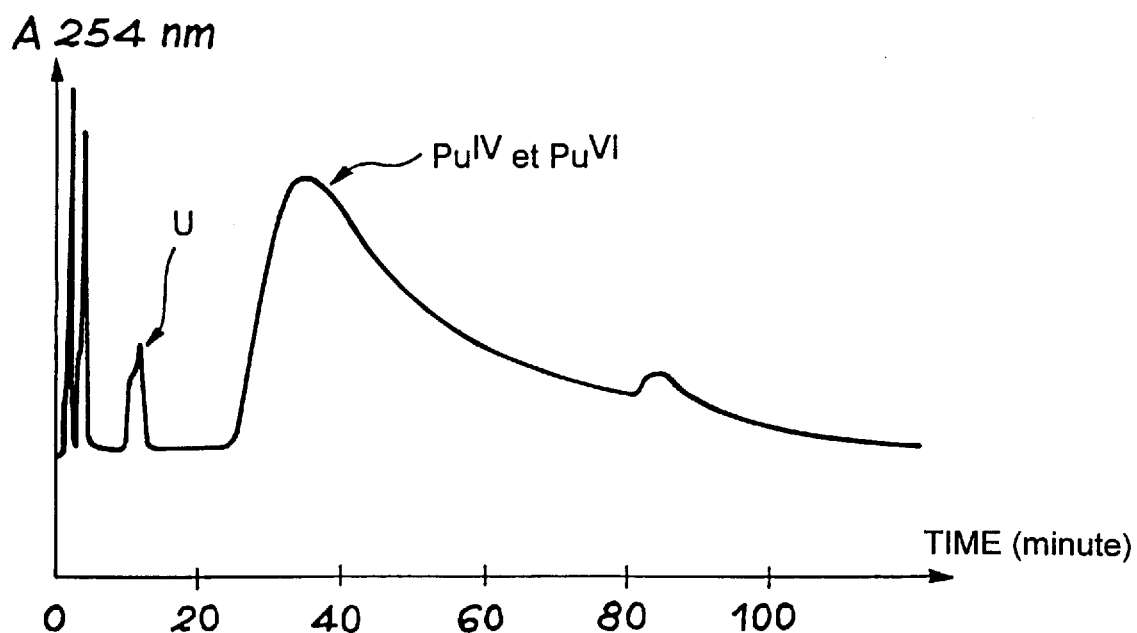
FIG. 3 represents a chromatogram of a solution of a mixture of uranium and plutonium obtained with the measurement method described by the prior art.

FIG. 3 represents, for purposes of comparison, the chromatogram obtained on the same solution using the measurement method described by Patent FR-A-2 691 542. This chromatogram clearly reveals that it is not possible to measure plutonium with the mobile phase of Patent FR-A-2 691 542 because the composition of the mobile phase and its excessively high pH cause the polymerization of the plutonium and render its integration impossible.

A comparison of FIGS. 2 and 3 reveals the advantages provided by the invention:

simultaneous measurement of at least one element chosen from among Pu (IV), Pu (VI), uranium and nitrates, improved selectivity of the peaks, good level of accuracy and reproducibility, measurement possible for quantities varying widely in elements of interest (from 0.001 g/l to 450 g/l).

We claim:

1. Process for measuring at least one of the elements chosen from among Pu (IV), Pu (VI), uranium and nitrates, present in a solution by liquid phase chromatography, characterized in that it comprises the following stages:
   a) injection of a sample of the solution on a stationary phase comprising an apolar-type support,
   b) elution of said sample by a mobile liquid phase which comprises a counter-ion of ammonium type, sulfate ion, an acid of a normality equal to or greater than 0.001N, a mixture of solvents comprising an alcohol in $C_1$–$C_4$, a polar modifying organic solvent different from an alcohol, miscible with water, and water, in order to obtain an eluate, and
   c) measurement of the eluate so as to determine the element(s) present in the solution to be analyzed and to measure this element or these elements.

2. Process according to claim 1, characterized in that the concentration of the element(s) in the eluate is measured by spectrophotometry.

3. Process according to claim 1, characterized in that said polar modifying organic solvent acts by dipole-dipole interaction.

4. Process according to claim 3, characterized in that said polar modifying organic solvent is tetrahydrofurane (THF) or dioxane.

5. Process according to claim 1, characterized in that said alcohol in $C_1$–$C_4$ is methanol (MeOH).

6. Process according to claim 1, characterized in that said counter-ion of ammonium type is the cetyltrimethylammonium ion ($CTA^+$).

7. Process according to claim 1, characterized in that said acid is sulfuric acid.

8. Process according to claim 1, characterized in that the mobile phase comprises in volume:
   about 60 to 65% of water,
   about 30% of methanol, and
   about 5 to 10% of tetrahydrofurane,
and contains about:
   0.05 mol/l of sulfuric acid,
   0.1 to 0.2 mol/l of ammonium sulfate, and
   0.005 mol/l of cetyltrimethylammonium.

9. Process according to claim 1, characterized in that said apolar-type stationary phase is selected from among a silica support grafted with organic molecules, a polymeric support and a carbon-based support.

10. Process according to claim 2, characterized by the simultaneous analysis by spectrophotometry at 254 nm and 230 nm of at least two elements chosen from among Pu (IV), Pu (VI), uranium and nitrate in the eluate.

11. Process according to claim 2, characterized in that the eluate is analyzed at 830 nm for Pu (VI).

* * * * *